United States Patent
Proia et al.

(10) Patent No.: US 11,497,733 B2
(45) Date of Patent: Nov. 15, 2022

(54) COMBINATION THERAPY OF HSP90 INHIBITORS AND PD-1 INHIBITORS FOR TREATING CANCER

(71) Applicant: Synta Pharmaceuticals Corp., Lexington, MA (US)

(72) Inventors: David A. Proia, Newton, MA (US); Patricia E. Rao, Acton, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 15/549,866

(22) PCT Filed: Feb. 9, 2016

(86) PCT No.: PCT/US2016/017075
§ 371 (c)(1),
(2) Date: Aug. 9, 2017

(87) PCT Pub. No.: WO2016/130502
PCT Pub. Date: Aug. 18, 2016

(65) Prior Publication Data
US 2018/0064689 A1    Mar. 8, 2018

Related U.S. Application Data

(60) Provisional application No. 62/113,807, filed on Feb. 9, 2015.

(51) Int. Cl.
| | | |
|---|---|---|
| A61K 39/00 | (2006.01) | |
| A61K 31/4196 | (2006.01) | |
| A61K 39/395 | (2006.01) | |
| A61K 31/6615 | (2006.01) | |
| C07K 16/28 | (2006.01) | |
| A61K 31/675 | (2006.01) | |
| C07K 16/30 | (2006.01) | |

(52) U.S. Cl.
CPC ...... *A61K 31/4196* (2013.01); *A61K 31/6615* (2013.01); *A61K 31/675* (2013.01); *A61K 39/3955* (2013.01); *A61K 39/39558* (2013.01); *C07K 16/2818* (2013.01); *C07K 16/2827* (2013.01); *C07K 16/3046* (2013.01); *A61K 2039/505* (2013.01); *A61K 2039/545* (2013.01); *C07K 2317/24* (2013.01); *C07K 2317/76* (2013.01)

(58) Field of Classification Search
CPC ............ A61K 31/4196; A61K 39/3955; A61K 31/675; A61K 39/39558; A61K 2039/505; C07K 16/2827; C07K 2317/76; A61P 43/00; A61P 35/00
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,529,925 A | 6/1996 | Morris et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 5,770,421 A | 6/1998 | Morris et al. | |
| 7,700,339 B2 | 4/2010 | Rikova et al. | |
| 8,168,757 B2 * | 5/2012 | Finnefrock | C07K 16/2896 530/387.1 |
| 9,827,309 B2 | 11/2017 | Strack et al. | |
| 2005/0176024 A1 | 8/2005 | McSwiggen et al. | |
| 2006/0167070 A1 | 7/2006 | Ying et al. | |
| 2011/0110923 A1 | 5/2011 | Lee et al. | |
| 2015/0202291 A1 * | 7/2015 | Bosch | A61K 35/15 424/156.1 |
| 2015/0210769 A1 * | 7/2015 | Freeman | C07K 16/2896 424/136.1 |

FOREIGN PATENT DOCUMENTS

| | | | | |
|---|---|---|---|---|
| JP | 2014520808 A | 8/2014 | | |
| WO | WO-2009023211 A1 | 2/2009 | | |
| WO | WO-2013006864 A2 * | 1/2013 | ......... | A61K 31/4196 |
| WO | WO-2013170159 A1 * | 11/2013 | ........... | A61K 39/395 |
| WO | WO-2013173223 A1 | 11/2013 | | |

OTHER PUBLICATIONS

Gabrilovich, Oncology,thelancet.com vol. 8 Jan. 2007, 2 pages (Year: 2007).*
Nomi et al. Clin. Cancer Res vol. 13 p. 2151 (2007), (Year: 2007).*
Anderson, "Laboratory methods for KRAS mutation analysis," Expert Rev Mol Diagn, 11(6):635-42 (Jul. 2011).
Balschun et al., "Detection of KRAS and BRAF mutations in advanced colorectal cancer by allele-specific single-base primer extension," Expert Rev Mol Diagn, 11(8):799-802 (Nov. 2011).
ClinicalTrials.gov identifier NCT01798485, "A Phase 3 Study of Ganetespib in Combination With Docetaxel Versus Docetaxel Alone in Patients With Advanced NSCLC (Galaxy 2)," https://clinicaltrials.gov/ct2/show/NCT01798485 (11 pages) (Feb. 2013).

(Continued)

*Primary Examiner* — Sheela J. Huff
(74) *Attorney, Agent, or Firm* — Dechert LLP; Andrea L. C. Reid; Joseph W. Arico

(57) ABSTRACT

A pharmaceutical composition comprising a PD-1 inhibitor and a Hsp90 inhibitor, or a tautomer, or a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole or 5-hydroxy-4-(5-hydroxy-4-(1-methyl-1H-indol-5-yl)-4H-1,2,4-triazol-3-yl)-2-isopropylphenyl dihydrogen phosphate. Also provided is a method for treating cancer in a subject in need thereof, using the pharmaceutical composition described herein.

13 Claims, 8 Drawing Sheets

(56) References Cited

OTHER PUBLICATIONS

Didelot, C. et al. "Anti-Cancer Therapeutic Approaches Based on Intracellular and Extracellular Heat Shock Proteins," Current Medicinal Chemistry, 14(27):2839-2847 (2007).
Fessas et al., "A molecular and preclinical comparison of the PD-1-targeted T-cell checkpoint inhibitors nivolumab and pembrolizumab," Semin Oncol, 44(2):136-140 (Apr. 2017).
Finberg et al., "Mucinous differentiation correlates with absence of EGFR mutation and presence of KRAS mutation in lung adenocarcinomas with bronchioloalveolar features," J Mol Diagn, 9(3):320-6 (Jul. 2007).
Fried et al., "Preliminary results of immune modulating antibody MDV9300 (pidilizumab) treatment in children with diffuse intrinsic pontine glioma," J Neurooncol, 136(1):189-195 (Jan. 2018 ).
Gleason et al., "Inflammatory myofibroblastic tumours: where are we now?" J Clin Pathol, 61(4):428-437 (Apr. 2008).
Goldman et al., "A first in human, safety, pharmacokinetics, and clinical activity phase I study of once weekly administration of the Hsp90 inhibitor ganetespib (STA-9090) in patients with solid malignancies," BMC Cancer, 13:152 (Mar. 2013).
Gullick, "Prevalence of aberrant expression of the epidermal growth factor receptor in human cancers," Br Med Bull, 47(1):87-98 (Jan. 1991).
Hamanishi et al., "Programmed cell death 1 ligand 1 and tumor-infiltrating CD8+ T lymphocytes are prognostic factors of human ovarian cancer," Proc Natl Acad Sci. USA, 27;104(9):3360-5 (Feb. 2007).
Hao et al. "Advances in targeted therapy for unresectable melanoma: New drugs and combinations," Cancer Letters, 359(1):1-8 (Apr. 2015).
International Search Report and Written Opinion issued by the European Patent Office as International Searching Authority for International Application No. PCT/US2016/017075 dated Apr. 18, 2016 (10 pages).
Jansen, A.P. et al. "Characterization of programmed cell death 4 in multiple human cancers reveals a novel enhancer of drug sensitivity," Molecular Cancer Therapeutics, 3(2):103-110 (2004).
Jhaveri et al., "A phase I trial of ganetespib in combination with paclitaxel and trastuzumab in patients with human epidermal growth factor receptor-2 (HER2)-positive metastatic breast cancer," Breast Cancer Res, 19(1):89 (Aug. 2017).
Jimeno et al., "KRAS mutations and sensitivity to epidermal growth factor receptor inhibitors in colorectal cancer: practical application of patient selection," J Clin Oncol, 1;27(7):1130-6 (Mar. 2009).
John et al., "Overview of molecular testing in non-small-cell lung cancer: mutational analysis, gene copy number, protein expression and other biomarkers of EGFR for the prediction of response to tyrosine kinase inhibitors," Oncogene, 28 Suppl 1:S14-23 (Aug. 2009).
Keytruda Center for Drug Evaluation and Research, Biological License Application #125514Orig1s000 (2014) 97 pages.
Keytruda Prescribing Information, Merck Sharp & Dohme Corp., Copyright 2014-2018, 52 pages.
Kim et al., "Prospects for targeting PD-1 and PD-L1 in various tumor types," Oncology (Williston Park), 28 Suppl 3:15-28 (Nov. 2014).
Koivunen et al., "EML4-ALK fusion gene and efficacy of an ALK kinase inhibitor in lung cancer," Clin Cancer Res, 14(13):4275-83 (Jul. 2008).
Lamant et al., "Non-muscle myosin heavy chain (MYH9): a new partner fused to ALK in anaplastic large cell lymphoma," Genes Chromosomes Cancer, 37(4):427-432 (Aug. 2003).
Lamy et al., "Metastatic colorectal cancer KRAS genotyping in routine practice: results and pitfalls," Mod Pathol, 24(8):1090-100 (Aug. 2011).
Lei et al., "Enhancement of chemosensitivity and programmed cell death by tyrosine kinase inhibitors correlates with EGFR expression in non-small cell lung cancer cells," Anticancer Res, 19(1A):221-8 (Jan.-Feb. 1999).
Li et al., "Development of anaplastic lymphoma kinase (ALK) small-molecule inhibitors for cancer therapy," Med Res Rev, 28(3):372-412 (May 2008).
Li et al., "Epitope mapping reveals the binding mechanism of a functional antibody cross-reactive to both human and murine programmed death," MABS, 9(4):628-637 (2017).
London et al., "Phase I evaluation of STA-1474, a prodrug of the novel HSP90 inhibitor ganetespib, in dogs with spontaneous cancer," PLoS One, 6(11):e27018 (Nov. 2011).
Mano, "Non-solid oncogenes in solid tumors: EML4-ALK fusion genes in lung cancer," Cancer Sci, 99(12):2349-55 (Dec. 2008).
Massarelli et al., "KRAS mutation is an important predictor of resistance to therapy with epidermal growth factor receptor tyrosine kinase inhibitors in non-small-cell lung cancer," Clin Cancer Res, 13(10):2890-6 (May 2007).
Modjtahedi et al., "The receptor for EGF and its ligands—expression, prognostic value and target for therapy in cancer (Review)," Int J Oncol, 4(2):277-96 (Feb. 1994).
Morère, "ASCO 2013: from the rediscovery of old recipes to targeted oncology," Targeted Oncology, 8(3):157-158 (Aug. 2013).
Okudela et al., "KRAS gene mutations in lung cancer: particulars established and issues unresolved," Pathol Int, 60(10):651-60 (Oct. 2010).
Opdivo Prescribing Information, Bristol-Myers Squibb, Revised Mar. and May 2019, 31 pages.
Ostrand-Rosenberg et al., "The Programmed Death-1 Immune Suppressive Pathway: Barrier to Anti-Tumor Immunity," J Immunol, 193(8): 3835-3841 (Oct. 2014).
Palmer et al., "Anaplastic lymphoma kinase signalling in development and disease," Biochem J, 420(3):345-61 (May 2009).
Pietzner et al., "Checkpoint-inhibition in ovarian cancer: rising star or just a dream?" J Gynecol Oncol, 29(6):e93 (Nov. 2018).
Pinto et al., "Comparison of methodologies for KRAS mutation detection in metastatic colorectal cancer," Cancer Genet, 204(8):439-46 (Aug. 2011).
Proia et al., "Targeting Heat-Shock Protein 90 (HSP90) as a Complementary Strategy to Immune Checkpoint Blockade for Cancer Therapy," Cancer Immunol Res, 3(6):583-9 (Jun. 2015) Also available online at cancerimmunolres.aacrjournals.org, doi: 10.1158/2326-6066.CIR-15-0057 (May 2015).
Pulford et al., "Anaplastic lymphoma kinase proteins in growth control and cancer," J Cell Physiol, 199(3):330-58 (2004).
Rekhtman et al., "Clarifying the spectrum of driver oncogene mutations in biomarker-verified squamous carcinoma of lung: lack of EGFR/KRAS and presence of PIK3CA/AKT1 mutations," Clin Cancer Res, 15;18(4):1167-76 (Feb. 2012).
Riely et al., "A phase 1 study of crizotinib and ganetespib (STA-9090) in ALK positive lung cancers," Journal of Clinical Oncology, 33:15 suppl:8064-8064 (2015) [Abstract only].
Rudzki et al., "ALK-positive diffuse large B-cell lymphoma: two more cases and a brief literature review," Pol J Pathol, 56(1):37-45 (2005).
Salomon et al., "Epidermal growth factor-related peptides and their receptors in human malignancies," Crit Rev Oncol Hematol, 19(3):183-232 (Jul. 1995).
Takeuchi et al., "KIF5B-ALK, a novel fusion oncokinase identified by an immunohistochemistry-based diagnostic system for ALK-positive lung cancer," Clin Cancer Res, 15(9):3143-3149 (May 2009).
Vakiani et al., "KRAS and BRAF: drug targets and predictive biomarkers," J Pathol, 223(2):219-29 (Jan. 2011).
Van Krieken et al., "KRAS mutation testing for predicting response to anti-EGFR therapy for colorectal carcinoma: proposal for an European quality assurance program," Virchows Arch, 453(5):417-31 (Nov. 2008).
Van Roy et al., "The emerging molecular pathogenesis of neuroblastoma: implications for improved risk assessment and targeted therapy," Genome Med, 27;1(7):74 (Jul. 2009).
Veale et al., "The relationship of quantitative epidermal growth factor receptor expression in non-small cell lung cancer to long term survival." Br J Cancer, 68(1):162-5 (Jul. 1993).

(56) References Cited

OTHER PUBLICATIONS

Wang, "Prognostic effect of programmed death-ligand 1 (PD-L1) in ovarian cancer: a systematic review, meta-analysis and bioinformatics study," J Ovarian Res, 12(1):37 (Apr. 2019).

Webb et el., "Anaplastic lymphoma kinase role in cancer pathogenesis and small-molecule inhibitor development for therapy," Expert Rev Anticancer Ther, 9(3):331-556 (Mar. 2009).

Weiss, J.M. et al. "Second-Line Therapy for Advanced NSCLC," the Oncologist, 18(8):947-953 (Aug. 2013).

Bae, et al., "Heat shock protein 90 is critical for regulation of phenotype and functional activity of human T lymphocytes and NK cells," J Immunol, 190(3):1360-71 (Feb. 2013).

Disis et al., "Avelumab (MSB0010718C), an anti-PD-L1 antibody, in patients with previously treated, recurrent or refractory ovarian cancer: A phase Ib, open-label expansion trial," Journal of Clinical Oncology. 2015; 33(15 Suppl.):5509. [Meeting Abstract only].

Gibney et al., "Predictive biomarkers for checkpoint inhibitor-based immunotherapy," Lancet Oncol. 2016; 17(12):e542-e551.

Hamanishi et al., "Safety and Antitumor Activity of Anti-PD-1 Antibody, Nivolumab, in Patients With Platinum-Resistant Ovarian Cancer," J Clin Oncol. 2015; 33(34):4015-22.

Ichiyanagi et al., "Essential role of endogenous heat shock protein 90 of dendritic cells in antigen cross-presentation," J Immunol. 2010, 185(5):2693-2700.

Ray-Coquard et al., "Part I of GANNET53: a European Multicenter Phase I/II Trial of the Hsp90 Inhibitor Ganetespib Combined With Weekly Paclitaxel in Women With High-Grade, Platinum-Resistant Epithelial Ovarian Cancer—A Study of the GANNET53 Consortium," Front Oncol. 2019; 9:832 (11 pages).

"Guidance for Industry: Estimating the Maximum Safe Starting Dose in Initial Clinical Trials for Therapeutics in Adult Healthy Volunteers," Food and Drug Adminisliation, Center for Drug Evaluation and Research (CDER), U.S. Department of Health and Human Services, Jul. 2005, 27 pages.

\* cited by examiner

*p = 0.0440

*p = 0.0036
**p = 0.0048
***p = 0.0182
****p = 0.0102
*****p = 0.0009

COMBINATION THERAPY OF HSP90 INHIBITORS AND PD-1 INHIBITORS FOR TREATING CANCER

RELATED APPLICATIONS

This application claims the benefit of U.S. Provisional Application No. 62/113,807, filed Feb. 9, 2015. The entire teachings of the aforementioned application are incorporated herein by reference.

BACKGROUND OF THE INVENTION

Harnessing the latent capacity of the immune system to control and/or eradicate human cancer has been a long-coveted, although elusive, frontier within the field of oncology. The primary goal of cancer immunotherapy is to trigger a self-sustaining cycle of immunity that is sufficient to amplify and propagate robust antitumor effects, and without inducing unrestrained autoimmune inflammatory responses. An increased understanding of the underlying mechanisms exploited by tumors in order to suppress adaptive immune responses and evade destruction has now translated into significant clinical advances using new classes of immunotherapeutic agents—particularly those that modulate immune checkpoint proteins, including cytotoxic T-lymphocyte antigen-4 (CTLA-4) and programmed death 1 (PD-1), immunoinhibitory receptors which serve to dampen tumor-associated T cell activation and effector responses, respectively. Indeed, it is now established that pharmacological blockade of such immune checkpoints, critical for the maintenance of self-tolerance but whose dysregulation by tumors serves as a major mechanism of immune resistance, can promote immunogenic antitumor activity in a manner showing enormous potential to revolutionize human cancer therapy.

A striking feature to emerge from the initial human trials evaluating monoclonal antibodies against CTLA-4 or PD-1 was a remarkable durability of response, even following treatment discontinuation, which in turn predicts for long-term patient survival. Moreover, antibody-mediated blockade of the ligand for PD-1, PD-L1, has also shown durable clinical benefits across multiple tumor types and these appeared superior to those achieved using conventional chemotherapeutic or molecularly-targeted approaches within the same indications. Conversely, however, the actual proportion of patients responding to these agents as monotherapy is typically low. As such, methods of enhancing the effectiveness of these therapies are still needed.

SUMMARY OF THE INVENTION

The present invention is based on the discovery that certain Hsp90 inhibitors and PD-1 inhibitors combinations are surprisingly effective in pre-clinical models with certain cancer cell types. The particular combination therapies disclosed herein demonstrate surprising biological activity with significant anticancer effects. Specifically, with the combination of Hsp90 inhibitors and PD-1 inhibitors, significant responses following PD-1/PD-L1 blockade have now been demonstrated in MC38 colon carcinoma and B16 melanoma cells.

The present teachings are directed, at least in part, to a method of treating cancer in a subject in need thereof, comprising (or consisting of) administering to the subject an effective amount of a PD-1 inhibitor (such as nivolumab, pembrolizumab, pidilizumab, BMS 936559, MPDL3280A, MSB0010718C or MEDI4736) and an effective amount of a Hsp90 inhibitor, or a tautomer, a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole, or 5-hydroxy-4-(5-hydroxy-4-(1-methyl-1H-indol-5-yl)-4H-1,2,4-triazol-3-yl)-2-isopropylphenyl dihydrogen phosphate. Preferably, the PD-1 inhibitor is nivolumab. Alternatively, the PD-1 inhibitor is pembrolizumab.

The PD-1 inhibitor and the Hsp90 inhibitor can be co-administered simultaneously (i.e., concurrently) as either separate formulations or as a combination formulation. Alternatively, they can be administered sequentially, as separate compositions. In one embodiment, first the Hsp90 inhibitor is administered, then the PD-1 inhibitor is administered to the subject in need thereof. In another embodiment, the PD-1 inhibitor is first administered, then the Hsp90 inhibitor is administered to the subject in need thereof.

The present teachings are also directed to a pharmaceutical composition comprising (or consisting of) a PD-1 inhibitor (such as nivolumab, pembrolizumab, pidilizumab, BMS 936559, MPDL3280A, MSB0010718C or MEDI4736) and a Hsp90 inhibitor, or a tautomer, or a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole or 5-hydroxy-4-(5-hydroxy-4-(1-methyl-1H-indol-5-yl)-4H-1,2,4-triazol-3-yl)-2-isopropylphenyl dihydrogen phosphate. Preferably, the PD-1 inhibitor is nivolumab. Alternatively, the PD-1 inhibitor is pembrolizumab.

In one embodiment, the present teachings are directed to a Hsp90 inhibitor, or a tautomer, or a pharmaceutically acceptable salt thereof, for use in the treatment of cancer in a subject in need thereof, in combination with a PD-1 inhibitor (such as nivolumab, pembrolizumab, pidilizumab, BMS 936559, MPDL3280A, MSB0010718C or MEDI4736) or a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole, or 5-hydroxy-4-(5-hydroxy-4-(1-methyl-1H-indol-5-yl)-4H-1,2,4-triazol-3-yl)-2-isopropylphenyl dihydrogen phosphate. Preferably, the PD-1 inhibitor is nivolumab. Alternatively, the PD-1 inhibitor is pembrolizumab.

In an embodiment, the present invention further provides the use of 3-(2,4-dihydroxy-5-isopropyl-phenyl)-4-(1-methyl-indol-5-yl)-5-hydroxy-[1,2,4]triazole, or a tautomer, or a pharmaceutically acceptable salt thereof, for the manufacture of a medicament for the treatment of a subject with cancer, in combination with a PD-1 inhibitor such as nivolumab, pembrolizumab, pidilizumab, BMS 936559, MPDL3280A, MSB0010718C or MEDI4736. Preferably, the PD-1 inhibitor is nivolumab. Alternatively, the PD-1 inhibitor is pembrolizumab.

In an embodiment, the present invention further provides the use of 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof, for the manufacture of a medicament for the treatment of a subject with cancer, in combination with a PD-1 inhibitor such as nivolumab, pembrolizumab, pidilizumab, BMS 936559, MPDL3280A, MSB0010718C or MEDI4736. Preferably, the PD-1 inhibitor is nivolumab. Alternatively, the PD-1 inhibitor is pembrolizumab.

In one alternative, the Hsp90 inhibitor and the PD-1 inhibitor can be administered in combination with another anti-cancer therapy. Alternatively, they are the only cancer therapeutics administered to the subject for the treatment of cancer in a subject in need thereof.

BRIEF DESCRIPTION OF THE DRAWINGS

The foregoing and other objects, features and advantages of the invention will be apparent from the following more particular description of some embodiments of the invention, as illustrated in the accompanying drawings. The drawings are not necessarily to scale, emphasis instead being placed upon illustrating the principles of the invention.

DETAILED DESCRIPTION OF THE INVENTION

Figure 1:
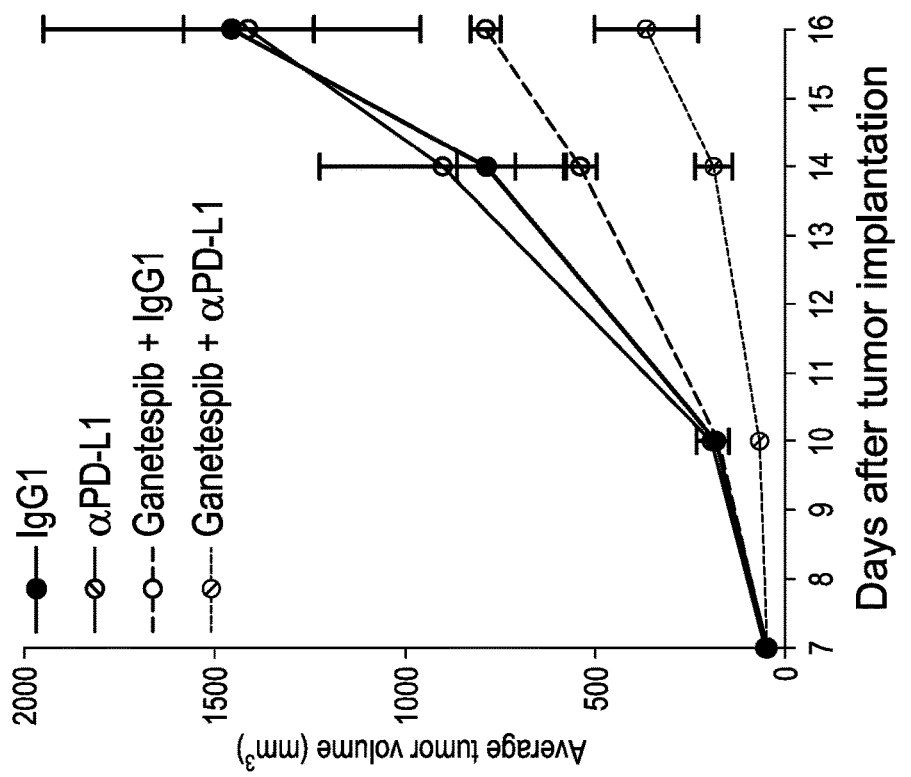
FIG. 1A shows a graph which indicate superior therapeutic indices achieved with ganetespib plus anti-PD-L1 antibody treatment in a PD-L1-expressing, syngeneic mouse model (i.e., MC38 colon carcinoma).
FIG. 1B shows a graph which indicates superior therapeutic indices achieved with ganetespib plus anti-PD-l1 antibody treatment in another PD-L1 expressing, syngeneic mouse model (i.e., B16 melanoma).
Figure 1:
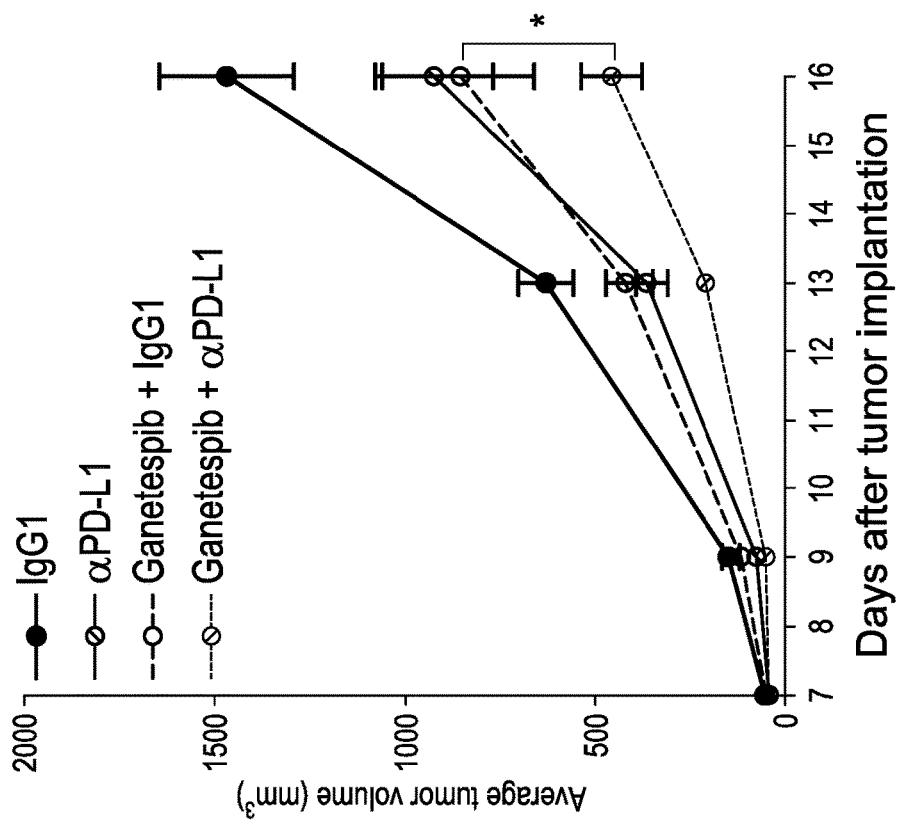

The invention is directed to a combination anti-cancer therapy comprising (or consisting of) an Hsp90 inhibitor (e.g., a compound listed in Table 1 below) and a PD-1 inhibitor.

Programmed cell death protein 1, also known as PD-1 and CD279 (cluster of differentiation 279), is a protein that in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2, both of which are members of the B7 family.

PD-1 and its ligands play an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells).

In a preferred embodiment, the PD-1 inhibitor binds programmed death ligand (PD-L1). In another preferred embodiment, the PD-1 inhibitor is an antibody.

Programmed death-ligand 1 (PD-L1) also known as cluster of differentiation 274 (CD274) or B7 homolog 1 (B7-H1) is a protein that in humans is encoded by the CD274 gene. Programmed death-ligand 1 (PD-L1) is a 40 kDa type 1 transmembrane protein that has been speculated to play a major role in suppressing the immune system during particular events such as pregnancy, tissue allografts, autoimmune disease and other disease states such as hepatitis. Normally the immune system reacts to foreign antigens where there is some accumulation in the lymph nodes or spleen which triggers a proliferation of antigen-specific CD8+ T cell. The formation of PD-1 receptor/PD-L1 or B7.1 receptor/PD-L1 ligand complex transmits an inhibitory signal which reduces the proliferation of these CD8+ T cells at the lymph nodes and supplementary to that PD-1 is also able to control the accumulation of foreign antigen specific T cells in the lymph nodes through apoptosis which is further mediated by a lower regulation of the gene Bcl-2. PD-L1 binds to its receptor, PD-1, found on activated T cells, B cells, and myeloid cells, to modulate activation or inhibition.

The PD-1 inhibitor used in the present invention includes, but is not limited to, nivolumab, pembrolizumab, pidilizumab, BMS 936559, MPDL3280A, MSB0010718C or MEDI4736. Among them, BMS 936559, MPDL3280A, MSB0010718C, and MEDI4736 bind ligand PD-L1, all of which are antibodies. Both nivolumab and pembrolizumab are approved by the Food and Drug Administration for treatment of unresectable or metastatic melanoma which no longer responds to other drugs.

As used herein, "Hsp90" includes each member of the family of heat shock proteins having a mass of about 90-kiloDaltons. For example, in humans the highly conserved Hsp90 family includes the cytosolic Hsp90α and Hsp90β isoforms, as well as GRP94, which is found in the endoplasmic reticulum, and HSP75/TRAP1, which is found in the mitochondrial matrix.

The Hsp90 inhibitors used in the present application are (i) 3-(2,4-dihydroxy-5-isopropyl-phenyl)-4-(1-methyl-indol-5-yl)-5-hydroxy-[1,2,4] triazole, or (ii) 5-hydroxy-4-(5-hydroxy-4-(1-methyl-1H-indol-5-yl)-4H-1,2,4-triazol-3-yl)-2-isopropylphenyl dihydrogen phosphate, the structures of these two compounds are shown in Table 1 below.

TABLE 1

| STRUCTURE | TAUTOMERIC STRUCTURE | NAME |
| --- | --- | --- |
| 1 | | 3-(2,4-DIHYDROXY-5-ISOPROPYL-PHENYL)-4-(1-METHYL-INDOL-5-YL)-5-HYDROXY-[1,2,4] TRIAZOLE (GANETESPIB) |

TABLE 1-continued

| STRUCTURE | TAUTOMERIC STRUCTURE | NAME |
|---|---|---|
| 1A 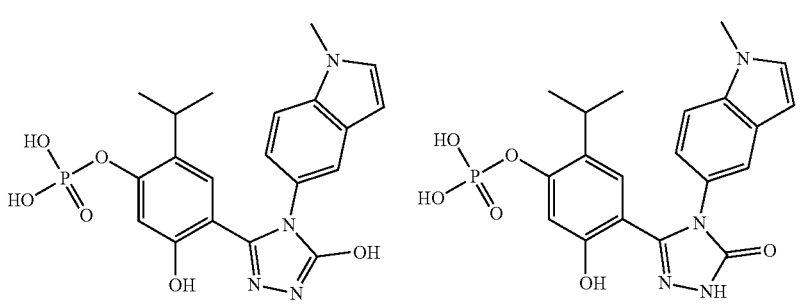 | | 5-HYDROXY-4-(5-HYDROXY-4-(1-METHYL-1H-INDOL-5-YL)-4H-1,2,4-TRIAZOL-3-YL)-2-ISOPROPYLPHENYL DIHYDROGEN PHOSPHATE |

The compounds described herein are defined by their chemical structures and/or chemical names. Where a compound is referred to by both a chemical structure and a chemical name, and the chemical structure and the chemical name conflict, the chemical structure is determinative of the compound's identity.

The Hsp90 inhibitory compounds used in the present invention can be prepared according to the methods and procedures disclosed in U.S. Patent Publication No. 2006/0167070, and WO2009/023211.

Notably, the triazolone compounds of the Hsp90 inhibitor typically can form a tautomeric structure as shown below and as exemplified by the tautomeric structures shown in Table 1:

The cancers can be treated in the present invention include esophageal cancer, bladder cancer, breast cancer, colon cancer, colorectal cancer, esophageal, gastric cancer, gastrointestinal stromal tumors (GIST), glioblastoma, hepatocellular cancer, lung cancer, melanoma, ocular melanoma, pancreatic cancer, prostate cancer, renal-cell cancer, or solid tumor. Preferably, the cancer is breast cancer, colon cancer, melanoma, non-small cell lung cancer, or renal-cell cancer. More preferably, the cancer is HER2-amplified breast cancer, colon cancer, melanoma, non-small cell lung cancer lacking EGFR mutations or anaplastic lymphoma kinase (ALK)-rearranged non-small cell lung cancer. Alternatively, the cancer is melanoma or colon cancer. In one embodiment, the cancer is adenocarcinoma, e.g. lung adenocarcinoma or colon adenocarcinoma.

In an embodiment, the method of treating a subject with cancer, wherein the subject has proven refractory to other therapies, includes administering to the subject an effective amount of a compound in Table 1, in combination with a PD-1 inhibitor such as nivolumab, pembrolizumab, pidilizumab, BMS 936559, MPDL3280A, MSB0010718C or MEDI4736, wherein the cancer is esophageal cancer, bladder cancer, breast cancer, colon cancer, colorectal cancer, esophageal, gastric cancer, gastrointestinal stromal tumors (GIST), glioblastoma, hepatocellular cancer, lung cancer, melanoma, ocular melanoma, pancreatic cancer, prostate cancer, renal-cell cancer, or solid tumor. In an embodiment, the cancer is breast cancer, colon cancer, melanoma, non-small cell lung cancer, or renal-cell cancer. In an embodiment, the cancer is HER2-amplified breast cancer, colon cancer, melanoma, non-small cell lung cancer lacking EGFR mutations or anaplastic lymphoma kinase (ALK)-rearranged non-small cell lung cancer. In an embodiment, the cancer is melanoma or colon cancer.

"Epidermal growth factor receptor" or "EGFR", as used herein, means any epidermal growth factor receptor (EGFR) protein, peptide, or polypeptide having EGFR or EGFR family activity (e.g., Her1, Her2, Her3 and/or Her4), such as encoded by EGFR Genbank Accession Nos. shown in Table I of U.S. Patent Application Publication No. US 2005-0176024, or any other EGFR transcript derived from a EGFR gene and/or generated by EGFR translocation. The term "EGFR" is also meant to include other EGFR protein, peptide, or polypeptide derived from EGFR isoforms (e.g., Her1, Her2, Her3 and/or Her4), mutant EGFR genes, splice variants of EGFR genes, and EGFR gene polymorphisms.

EGFR is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor α (TGFα), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

A number of human malignancies are associated with aberrant or overexpression of EGFR and/or overexpression of its specific ligands. Gullick, Br. Med. Bull. (1991), 47:87-98; Modijtahedi & Dean, Int. J. Oncol. (1994), 4:277-96; Salomon, et al., Crit. Rev. Oncol. Hematol. (1995), 19:183-232. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., Anti-cancer Res. (1999), 19:221-28; Veale, et al., Br. J.

Cancer (1993); 68:162-65. Mutations in EGFR are associated with many types of cancer as well. For example, EGFR mutations are highly prevalent in non-mucinous BAC patients. Finberg, et al., *J. Mol. Diagnostics* (2007) 9(3): 320-26.

The anaplastic lymphoma kinase (ALK) tyrosine kinase receptor is an enzyme that in humans is encoded by the ALK gene. The 2;5 chromosomal translocation is frequently associated with anaplastic large cell lymphomas (ALCLs). The translocation creates a fusion gene consisting of the ALK (anaplastic lymphoma kinase) gene and the nucleophosmin (NPM) gene: the 3' half of ALK, derived from chromosome 2, is fused to the 5' portion of NPM from chromosome 5. The product of the NPM-ALK fusion gene is oncogenic. Other possible translocations of the ALK gene, such as the eml4 translocation, are also implicated in cancer.

The general role of ALK in cancer has been described. See, e.g., Pulford et al., J. Cell Physiol. 199(3): 330-358 (2004). Abnormalities in the anaplastic lymphoma kinase (ALK) gene have an established pathogenic role in many pediatric and adult cancers, including non-small cell lung cancer (NSCLC), diffuse large B-cell lymphoma (DLBCL), anaplastic large cell lymphoma (ALCL), neuroblastoma (NBL), and inflammatory myofibroblastic tumors (IMT), non-Hodgkin's lymphoma (NHL), and esophageal squamous cell carcinoma (ESCC). These diseases account for more than 250,000 new cancer diagnoses each year in the United States alone.

More particularly, EML4-ALK and KIF5B-ALK translocations have been found in non-small cell lung cancer. See. e.g. Mano H., Cancer Sci. 2008 December; 99(12):2349-55; Takeuchi K et al., Clin Cancer Res. 2009 May 1; 15(9): 3143-9. CLTC-ALK mutation has been found in DLBCL. See e.g. Rudzki Z et al., Pol J Pathol. 2005; 56 (1):37-45. NPM-ALK, MSN-ALK, and other mutations have been found in ALCL. See e.g. Lamant L et al., Genes Chromosomes Cancer. 2003 August; 37 (4):427-32; Webb T R et al. Expert Rev Anticancer Ther 2009 March; 9(3):331-56. TPM4-ALK mutation has been found in esophageal squamous cell carcinoma (ESCC). See e.g. Li R, Morris S W., Med Res Rev. 2008 May; 28 (3):372-412. F1174L, R1275Q, and other point mutations have been found in NBL. See e.g. van Roy N et al. Genome Med 2009 Jul. 27; 1 (7):74. TPM3-ALK, TPM4-ALK, CLTC-ALK, RanBP2-ALK, and TPM4-ALK mutations have been found in IMT. See e.g. Gleason B C, Hornick J L. J Clin Pathol 2008 April; 61(4):428-37. The methods of detection and identification of these alterations, mutations or rearrangements in an ALK gene or gene product can be found in those above-identified references and references cited therein.

The methods and procedures for the detections and/or identifications of EGFR, and/or ALK over-expressions and/or mutations are known in the literature and can be easily carried out by a skilled person. See, e.g., U.S. Pat. Nos. 7,700,339; 5,529,925; 5,770,421; U.S. Patent Application Publication No. US2011/0110923; Palmer et al, Biochem. J. (2009), 345-361; Koivunen et al, *Clin. Can. Res.*, 2008, 14, 4275-4283; Anderson, *Expert Rev. Mol. Diagn.* 11(6), 635-642 (2011); Pinto et al, *Cancer Genetics* 204 (2011), 439-446; Rekhtman et al; *Clin Cancer Res* 2012; 18:1167-1176; Massarelli et al, *Clin Cancer Res* 2007; 13:2890-2896; Lamy et al, *Modern Pathology* (2011) 24, 1090-1100; Balschun et al, *Expert Rev. Mol. Diagn.* 11(8), 799-802 (2011); Vakiani et al, *J Pathol* 2011; 223, 219-229; Okudela et al, *Pathology International* 2010; 60: 651-660; John et al, *Oncogene* (2009) 28, S14-S23; Jimeno et al, *J. Clin. Oncol.* 27, 1130-1135 (2009); Van Krieken et al, *Virchows Archiv.* 453, 417-431 (2008); and the references cited in the-above identified references. Thresholds of increased expression that constitute an EGFR mutation or an ALK mutation are well known in the art. Moreover, it is generally recognized that if there is an ALK mutation detected in a cancer, it is extremely rare that an EGFR mutation will be implicated. Stated another way, once an ALK mutation is positively identified in a cancer, no further identification is necessary for EGFR mutation in the same cancer.

As used herein, the term "a pharmaceutically acceptable salt" refers to a salt prepared from a Hsp90 inhibitor (e.g., a compound listed in Table 1 below) or a PD-1 inhibitor having an acidic functional group, such as a carboxylic acid functional group, and a pharmaceutically acceptable inorganic or organic base. Suitable bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "a pharmaceutically acceptable salt" also refers to a salt prepared from a compound in Table 1 having a basic functional group, such as an amine functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, isonicotinic acid, oleic acid, tannic acid, pantothenic acid, saccharic acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, pamoic acid and p-toluenesulfonic acid.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In an embodiment, the subject is a non-human animal such as a farm animal (e.g., a horse, cow, pig or sheep), or a pet (e.g., a dog, cat, guinea pig or rabbit). In another embodiment, the subject is a human.

As used herein, the terms "therapies" and "therapy" can refer to any protocol(s), method(s), and/or agent(s) that can be used in the treatment, management, or amelioration of cancer or one or more symptoms thereof.

As used herein, the term "in combination" refers to the use of more than one therapeutic agent. The use of the term "in combination" does not restrict the order in which the therapeutic agents are administered to a subject with a disease or disorder, e.g., a cancer. A first therapeutic agent, such as a Hsp90 inhibitor, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as a PD-1 inhibitor, to a subject with cancer. In an embodiment, the Hsp90 inhibitor and the PD-1 inhibitor are dosed on independent schedules. In another embodiment, the Hsp90 inhibitor and the PD-1 inhibitor are dosed on approximately the same schedule.

The therapeutic agents of the combination therapies described herein can be administered sequentially or concurrently. In an embodiment, the administration of the Hsp90 inhibitor and the PD-1 inhibitor are done concurrently (simultaneously). In another embodiment, the administration of the Hsp90 inhibitor and the PD-1 inhibitor are done separately. In another embodiment, the administration of the Hsp90 inhibitor and the PD-1 inhibitor are done sequentially. In an embodiment, the administration of the Hsp90 inhibitor and the PD-1 inhibitor are done until the cancer is cured or stabilized or improved.

As used herein, the term "effective amount" refers to an amount of a compound described herein which is sufficient to reduce or ameliorate the severity, duration, progression, retard the advancement of cancer, cause the regression of cancer, or progression of a symptom associated with cancer, or enhance or improve the therapeutic effect(s) of another therapy. The precise amount of compound administered to a subject will depend on the mode of administration, the type and severity of the disease or condition and on the characteristics of the subject, such as general health, age, sex, body weight and tolerance to drugs. The skilled artisan will be able to determine appropriate dosages depending on these and other factors. When co-administered with other therapeutic agents, e.g., when co-administered with a PD-1 inhibitor, an "effective amount" of the PD-1 inhibitor will depend on the type of drug used. Suitable dosages are known for approved therapeutic agents and can be adjusted by the skilled artisan according to the condition of the subject, the type of condition(s) being treated and the amount of a compound of the invention being used. In cases where no amount is expressly noted, an effective amount should be assumed. Non-limiting examples of an effective amount of a compound described herein are provided herein below.

The dosage of an individual PD-1 inhibitor used in the pharmaceutical combination may be equal to or lower than the dose of an individual therapeutic agent when given independently to treat, manage, or ameliorate a disease or disorder, or one or more symptoms thereof. In an embodiment, the PD-1 inhibitor nivolumab or pembrolizumab is administered at a dose of between about 100 mg/m$^2$ to about 200 mg/m$^2$ by IV or orally once weekly, or once biweekly per treatment cycle. In an embodiment, nivolumab or pembrolizumab is administered once weekly. In an embodiment, nivolumab or pembrolizumab is administered at 125 mg/m$^2$ once weekly or 180 mg/m$^2$ once biweekly for the length of the treatment in a particular cycle. A treatment cycle can last between one and 6 weeks. The recommended dosages of therapeutic agents currently used for the treatment, management, or amelioration of a disease or disorder, or one or more symptoms thereof, can obtained from any reference in the art. For a more in depth review of dosage and treatment schedules for various disorders, see, e.g., GOODMAN & GILMAN'S THE PHARMACOLOGICAL BASIS OF BASIS OF THERAPEUTICS 9$^{TH}$ ED, (Hardman, et al., Eds., NY:Mc-Graw-Hill (1996)); PHYSICIAN'S DESK REFERENCE 57$^{TH}$ ED. (Medical Economics Co., Inc., Montvale, N.J. (2003)).

In another embodiment, the method of treating a subject with cancer includes administering to the subject an amount of a Hsp90 inhibitor described herein, or a tautomer, or a pharmaceutically acceptable salt thereof, in combination with an amount of between about 100 mg/m$^2$ to about 200 mg/m$^2$ of PD-1 inhibitor. In an embodiment, the Hsp90 inhibitor is in the amount of 2 mg/m$^2$ to about 260 mg/m$^2$, e.g., about 75 mg/m$^2$, about 85 mg/m$^2$, about 100 mg/m$^2$, about 110 mg/m$^2$, about 115 mg/m$^2$, about 120 mg/m$^2$, about 145 mg/m$^2$, about 150 mg/m$^2$, about 175 mg/m$^2$, about 180 mg/m$^2$, about 200 mg/m$^2$, about 215 mg/m$^2$ or about 260 mg/m$^2$. It is believed that the disclosed combination therapy can in some instances result in a synergistic anti-cancer effect.

In general, the recommended daily dose range of a Hsp90 inhibitor for the conditions described herein lie within the range of from about 0.01 mg to about 1000 mg per day, given as a single once-a-day dose preferably as divided doses throughout a day. In an embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

In a specific embodiment, the invention provides a method of treating cancer in a subject, the method comprising administering to a subject in need thereof a dose of the Hsp90 inhibitor at least 150 µg/kg, at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, once every 2 days, once every 3 days, once every 4 days, once every 5 days, once every 6 days, once every 7 days, once every 8 days, once every 10 days, once every two weeks, once every three weeks, or once a month.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Different therapeutically effective amounts may be applicable for different cancers, as will be readily known by those of ordinary skill in the art. Similarly, amounts sufficient to manage, treat or ameliorate such cancers, but insufficient to cause, or sufficient to reduce, adverse effects associated with the Hsp90 inhibitor described herein are also encompassed by the above described dosage amounts and dose frequency schedules. Further, when a patient is administered multiple dosages of a Hsp90 inhibitor described herein, not all of the dosages need be the same. For example, the dosage administered to the patient may be increased to improve the therapeutic effect of the compound or it may be decreased to reduce one or more side effects that a particular patient is experiencing.

In some embodiments, the present invention provides pharmaceutical composition for treating cancer in a subject in need thereof. In a specific embodiment, the composition comprises 3-(2,4-dihydroxy-5-isopropyl-phenyl)-4-(1-methyl-indol-5-yl)-5-hydroxy-[1,2,4] triazole, or 5-hydroxy-4-(5-hydroxy-4-(1-methyl-1H-indol-5-yl)-4H-1,2,4-triazol-3-yl)-2-isopropylphenyl dihydrogen phosphate, or a tautomer or a pharmaceutically acceptable salt thereof, in combination of a PD-1 inhibitor, and a pharmaceutically acceptable carrier.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON, J. P., REMINGTON'S PHARMACEUTICAL SCIENCES (Mack Pub. Co., 17$^{th}$ ed., 1985). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate, and the like. Methods for encapsulating compositions, such as in a coating of hard gelatin or cyclodextran, are known in the art. See BAKER, ET AL., CONTROLLED RELEASE OF BIOLOGICAL ACTIVE AGENTS, (John Wiley and Sons, 1986).

In an embodiment, the composition includes a pharmaceutical composition or a single unit dosage form containing both an Hsp90 inhibitor and a PD-1 inhibitor. Pharmaceutical composition and dosage forms described herein comprise the two active ingredients in relative amounts and formulated in such a way that a given pharmaceutical composition or dosage form can be used to treat cancer. Preferred pharmaceutical composition and dosage forms comprise a compound in Table 1, or a tautomer or pharmaceutically acceptable salt thereof, in combination with a PD-1 inhibitor. Optionally, these embodiments can also contain one or more additional anticancer chemotherapeutic agents.

The pharmaceutical composition described herein are formulated to be compatible with its intended route of administration. Examples of routes of administration include parenteral, e.g., intravenous, intradermal, subcutaneous, oral, intranasal (e.g., inhalation), transdermal (topical), transmucosal, and rectal administration. In a specific embodiment, the combination is formulated in accordance with routine procedures as a pharmaceutical composition adapted for intravenous, subcutaneous, intramuscular, oral, intranasal or topical administration to human beings. In an embodiment, the combination is formulated in accordance with routine procedures for subcutaneous administration to human beings.

The Hsp90 inhibitor described herein can be also formulated into or administered by controlled release means or by delivery devices that are well known to those of ordinary skill in the art. Examples include those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566.

The invention can be understood more fully by reference to the following illustrative examples, which are intended to exemplify non-limiting embodiments of the invention.

EXAMPLES

Example 1

As indicated in FIG. 1, superior therapeutic indices were achieved with combination ganetespib plus anti-PD-L1 antibody treatment in two PD-L1-expressing, syngeneic mouse models. In allograft tumors derived from MC38 colon carcinoma cells, ganetespib monotherapy induced a comparable degree of tumor growth suppression to that seen following selective anti-PD-L1 antibody treatment; combining both agents resulted in a significant improvement in antitumor efficacy. Further, antibody administration alone was largely ineffective at inhibiting B16 melanoma tumor growth. However, ganetespib co-therapy strongly potentiated the tumor response in this highly aggressive cancer model. Such findings support the premise that targeting HSP90 may represent a complementary and therapeutically advantageous approach together with immune checkpoint blockade for augmenting antitumor immune responses.

The HSP90 inhibitor ganetespib potentiates the antitumor efficacy of PD-L1 antibody treatment in syngeneic mouse tumor models. In FIG. 1 (a), C57 BL/6 mice bearing established MC38 colon carcinoma tumors (n=7/group) were treated with 200 μg IgG1 control or anti-PD-L1 antibody (αPD-L1; Sorrento Therapeutics, Inc., San Diego), either alone or in combination with 125 mg/kg ganetespib. Ganetespib was dosed on a weekly schedule (days 8 and 15), αPD-L1 was administered on days 8, 12, and 15. The combination of ganetespib plus αPD-L1 displayed significantly greater antitumor activity than either individual agent (*P<0.02). In FIG. 1 (b), C57 BL/6 mice bearing established B16 melanoma tumors (n=3/group) were dosed using a similar regimen as in (a). While administration of αPD-L1 alone had no effect on tumor growth, the efficacy of antibody treatment was potentiated by co-treatment with ganetespib.

Example 2

Female C57 BL/6 mice (Charles River Laboratories, Wilmington, Mass.) at 7-12 weeks of age were maintained in a pathogen-free environment. Mouse MC38 colon carcinoma cells (provided by Sorrento Therapeutics, San Diego, Calif.) were subcutaneously implanted into C57 BL/6 mice at 1×10E5 per mouse on Day 0. Seven days after implantation, mice bearing established tumors (101-162 mm3) were randomized into treatment groups of 6. The following day, mice were dosed with either vehicle [DRD (10% DMSO, 18% Cremophor RH 40, 3.6% dextrose, i.v.)], rat IgG2a (Bio-X-Cell; 10 mg/kg, i.p.), anti-mouse PD-1 IgG2a (Bio-X-Cell; 10 mg/kg, i.p.), or ganetespib (125 mg/kg formulated in DRD, i.v.) using the schedules and regimens indicated. Fourteen days later (Day 22) tumors were resected sterilely from all animals and placed into PBS.

Tumors were resected from all animals on the same day of study, 3 days after the last ganetespib dosing. Tumors were diced into 3 mm pieces in DMEM+10% FCS (Dulbecco's modified Eagle's medium containing 10% foetal calf serum) and incubated overnight to release tumor infiltrating lymphocytes (TIL). TIL were collected with the media from each well, filtered through nylon mesh to remove tumor fragments and centrifuged. Red blood cells (RBC) were removed by lysis with Ammonium-Chloride-Potassium (ACK) lysing buffer and the total number of recovered cells were counted. TIL were stained for flow cytometry using 2 staining cocktails; CD4 FITC/CD16 PE/CD25 PerCP Cy5.5, CD8 PE Cy7, CD45 APC, CD19

APC Cy7, or CD8 PE Cy7, CD4 PerCP Cy5.5 and CD45 APC Cy7. Tubes stained with the second staining cocktail were fixed and permeabilized using the Becton Dickinson Transcription Factor Buffer kit and then stained with anti-granzyme B Alexafluor 647 and FOXP3 Alexafluor 488. Analysis was performed on a Becton Dickinson LSRII using FACSDiva software. To determine the percent of each cell type. The total number of each cell type was calculated from the percentage of the cell type and the total number of TIL/sample. TIL/cu mm of tumor were calculated from the total number of each type of cell and the calculated volume of each tumor.

Figure 2:
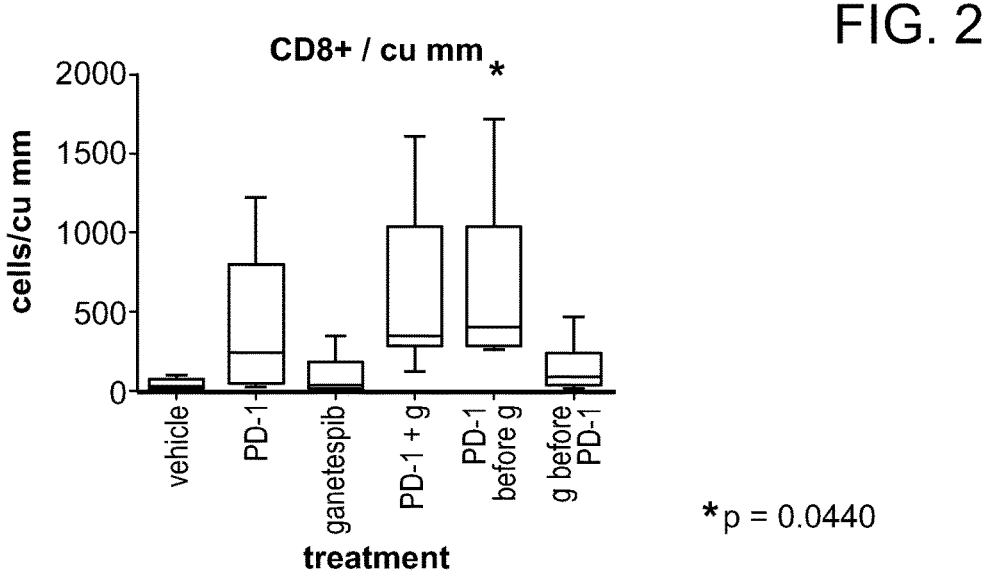
FIGS. 2-4 demonstrate tumor infiltrating lymphocytes created in mice with MC38 tumors after treating with PD-1 antibodies and/or ganetespib. Box and Whisker plots show the median as a bar inside the box; the box indicates the 25th and 75th percentile of the data points and the whiskers indicate the minimum and maximum data points.
Figure 2:
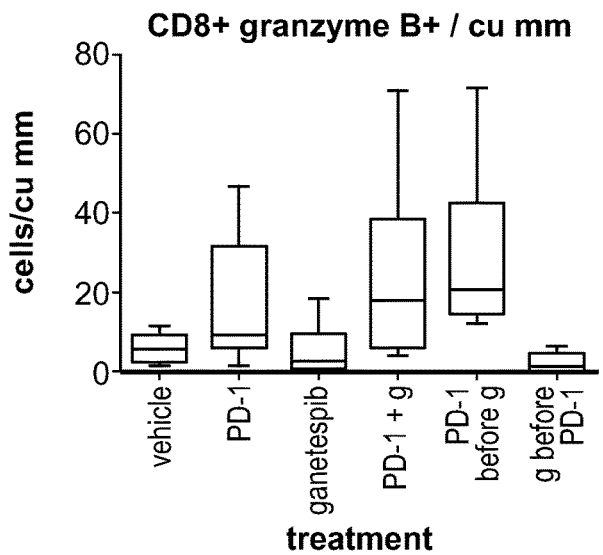
Figure 2:
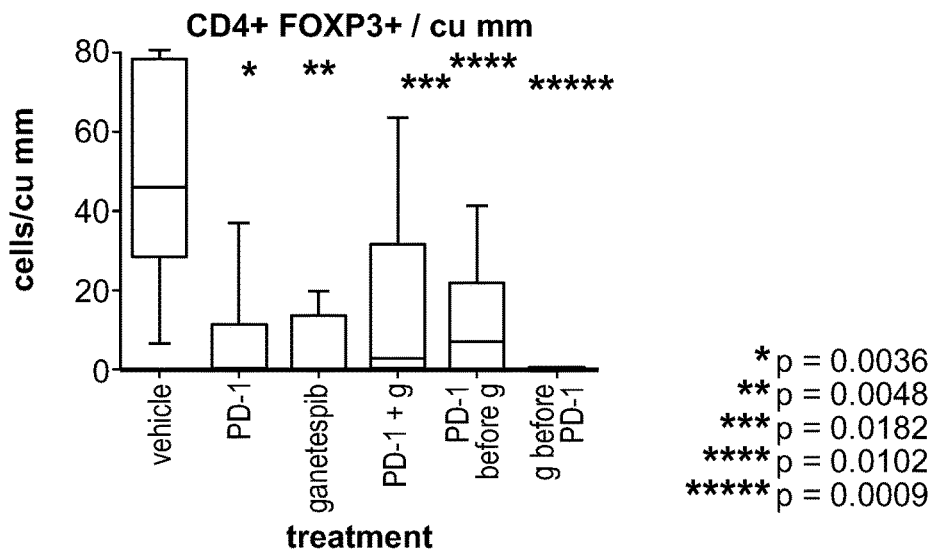
Figure 3:
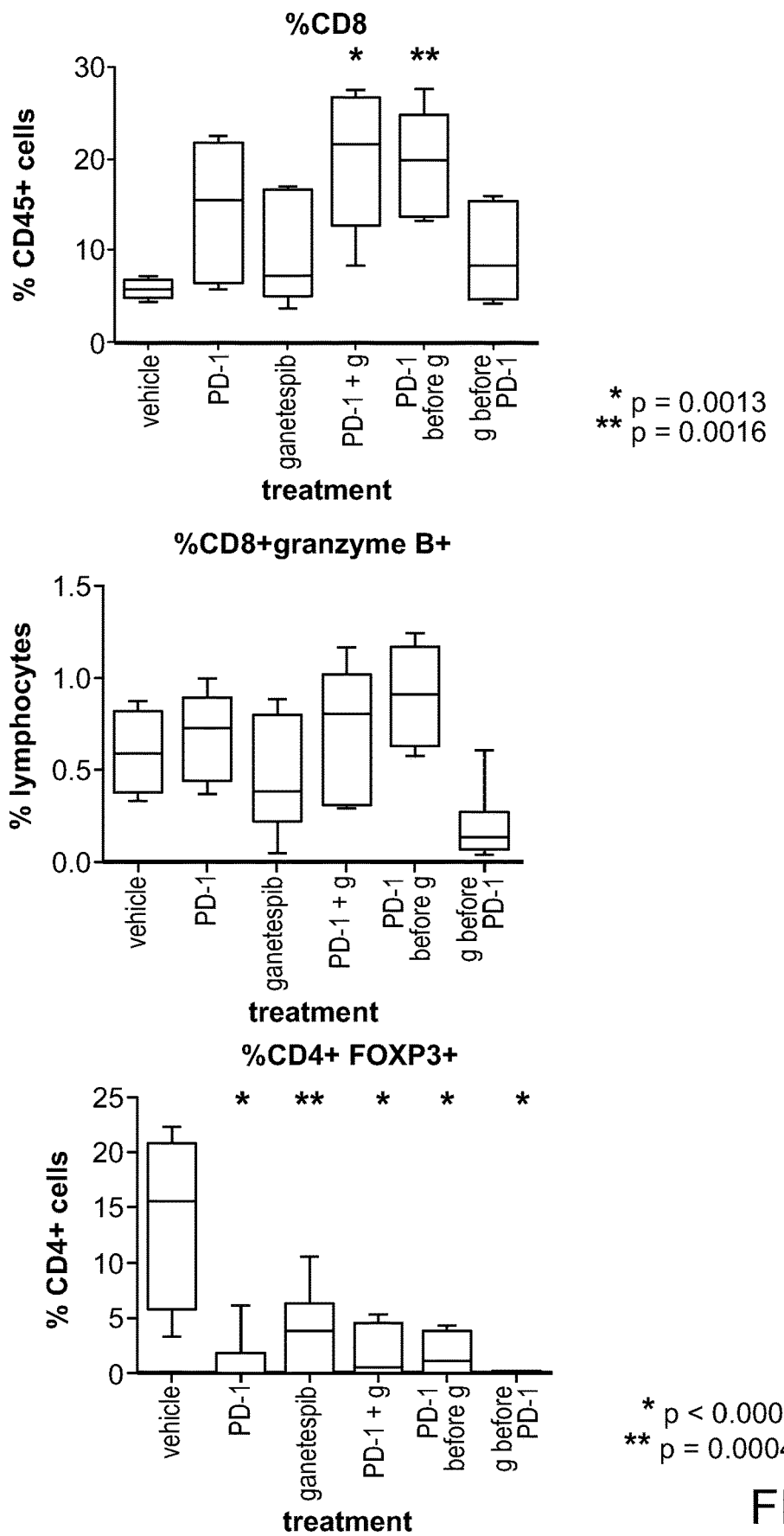
Figure 4:
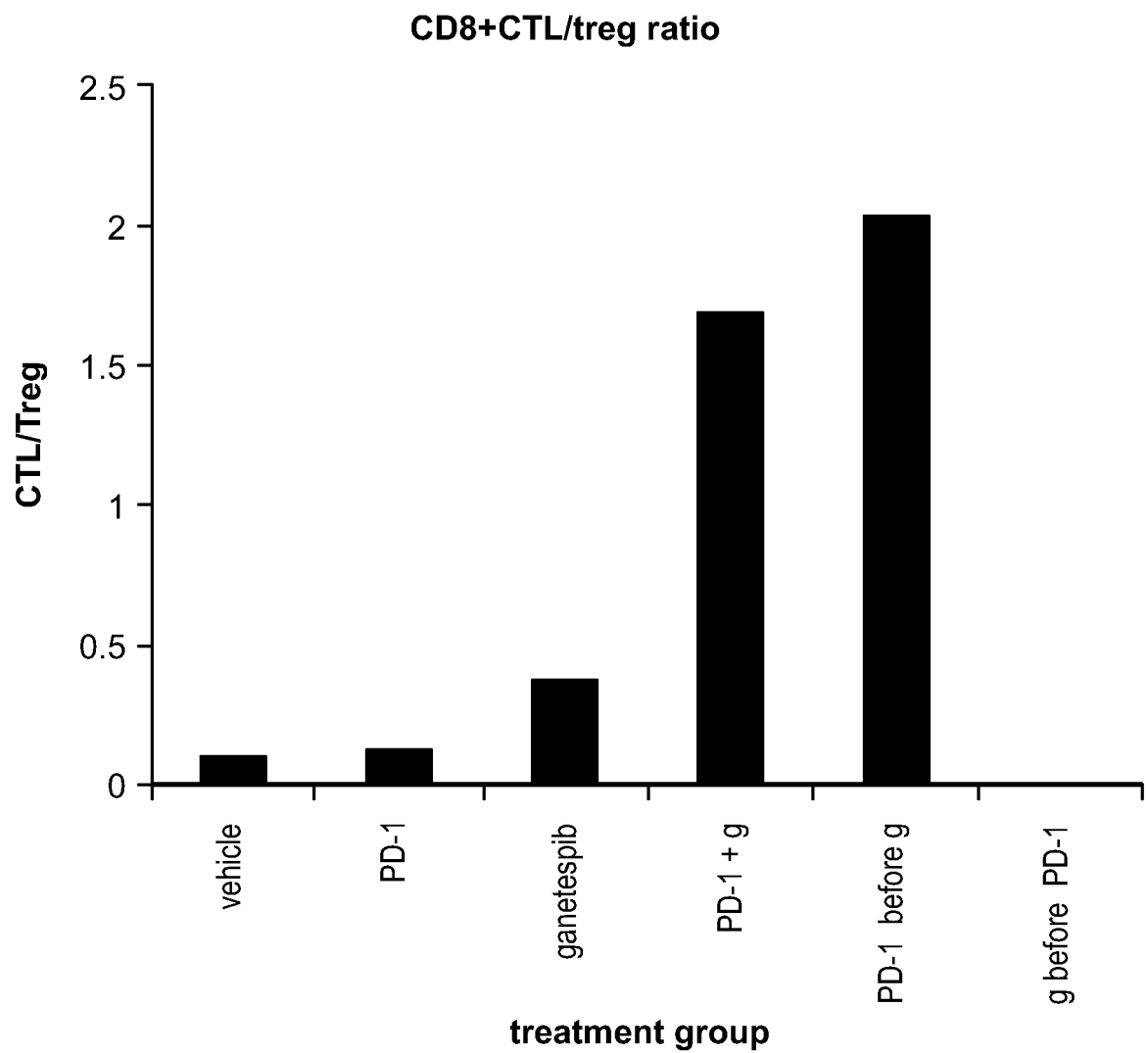

The results are shown in FIGS. 2-4, which demonstrate that tumor infiltrating lymphocytes from mice with MC38 tumors treated with PD-1 antibodies and ganetespib contained more CD8+ cells, fewer CD4+CD25+ or CD4+ FOXP3+ regulatory T cells, and a higher CD8+ CTL/Treg ratio, than mice from tumors treated with PD-1 or PD-L1 alone. Notably, CD8+ T cells are T cells which respond to antigen presented by MHC Class I and can differentiate into Cytotoxic T lymphocytes (CTL). CD8+ granzyme B+cells are CTL. CD4+FOXP3+ are regulatory T cells which can prevent effector T cells (like CTL) from attacking the tumor.

CD8+CTL/Treg ratio in TIL was calculated from the ratio of the number of CD8+granzyme b+ cells to the number of CD4+FOXP3+ cells in each sample. The means are shown in FIG. 4. No data are shown for ganetespib before PD-1 because too few CD4+FOXP3+ cells were found in these samples for calculations.

Example 3

TIL, collected as described in Example 2 were mixed with MC-38 or CT-26 tumor cells labeled with Calcein-AM at a ratio of 250:1 (CT26 tumor experiment) or 200:1 (MC38 experiment) in triplicate and incubated for 5 hrs at 37 degrees. Supernatant was collected from each assay well and released Calcein-AM measured by measuring fluorescence at 535 nm. Spontaneous release from tumor cells incubated with no lymphocytes and total release from tumor cells lysed by addition of Triton X-100 were used to calculate % specific lysis.

Figure 5:
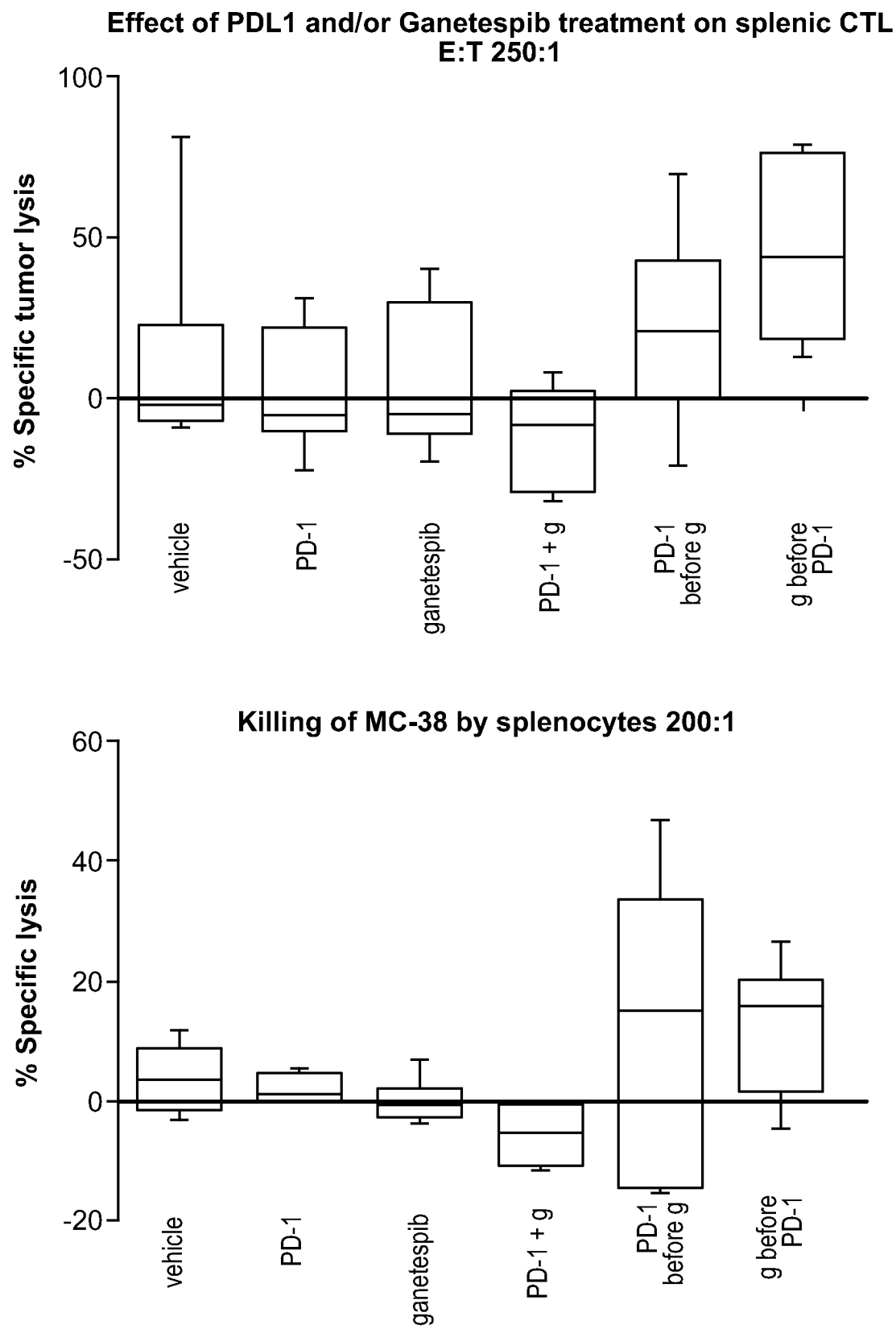
FIG. 5 demonstrates that splenocytes from mice bearing MC38 tumors treated with combination of ganetespib and PD-1 antibodies contained more Cytotoxic T lymphocytes (CTL) than splenocytes from control or PD-1 only treated animals, suggesting an enhancement of central anti-tumor immunity by the addition of ganetespib treatments to PD-1 antibody treatment.

The results are shown in FIG. 5. Splenocytes from mice bearing MC38 tumors treated with combination of ganetespib and PD-1 antibodies contained more CTL than splenocytes from control or PD-1 only treated animals, suggesting an enhancement of central anti-tumor immunity by the addition of ganetespib treatments to PD-1 antibody treatment.

Example 4

Mice with MC38 tumors received a dose of ganetespib. Tumors (3 per time point) were removed from the animals at 4, 24, 48 and 120 hr post dose. RNA was prepared and analyzed for gene expression using NanoString. Expression levels of genes were made by comparing drug treated tumors with vehicle-treated tumors.

Figure 6:
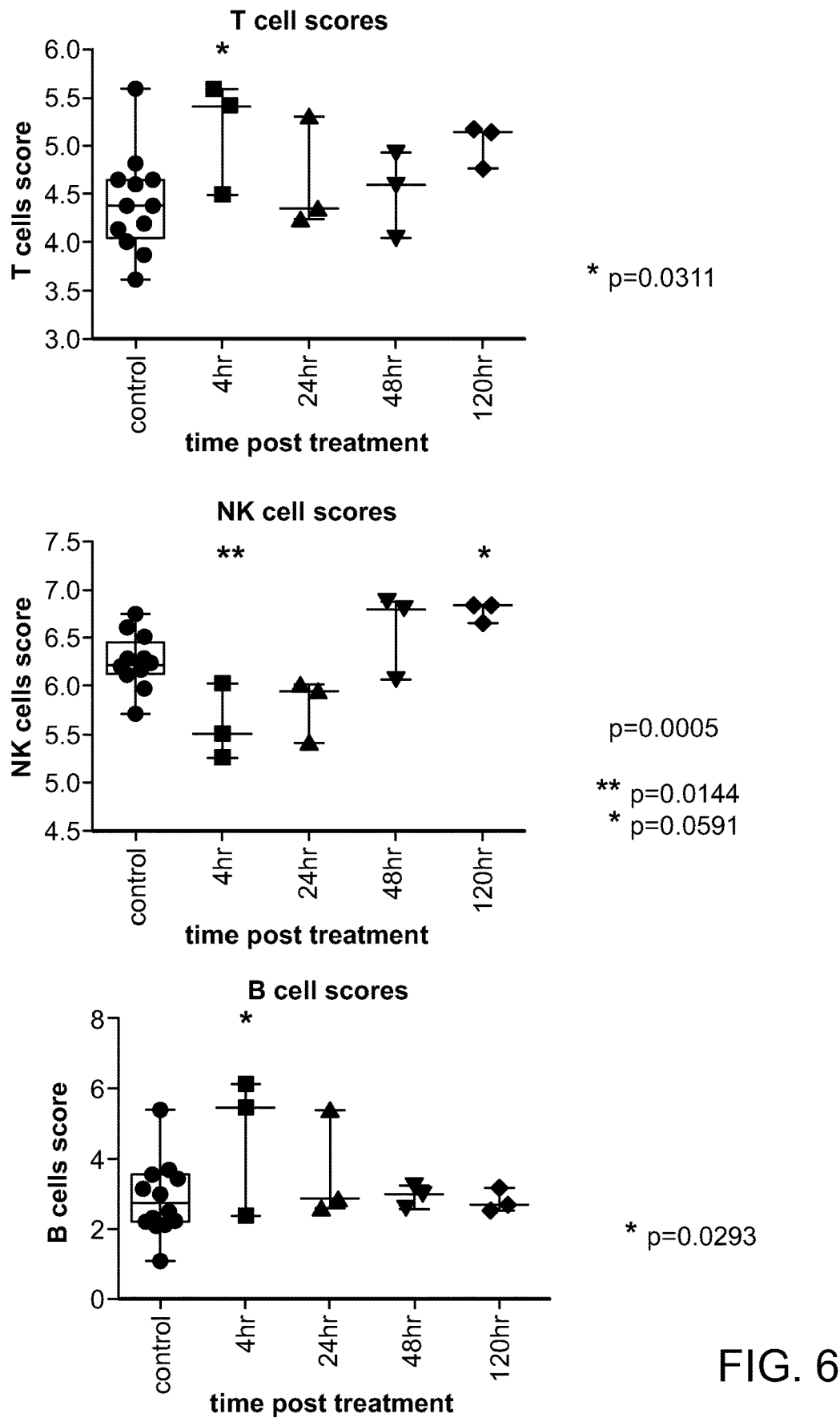
FIG. 6 shows the results of gene expression array.

Gene expression arrays confirmed that within 48-120 hr after in vivo treatment of MC38 tumors with ganetespib increased numbers of NK cells and CD8 cells and decreased Treg cells. Increases in a large number of chemokines were also found. As reflected in FIG. 6, gene expression demonstrates influx of T cells, B cells and NK cells into tumors after a single ganetespib administration.

Example 5

Figure 7A:
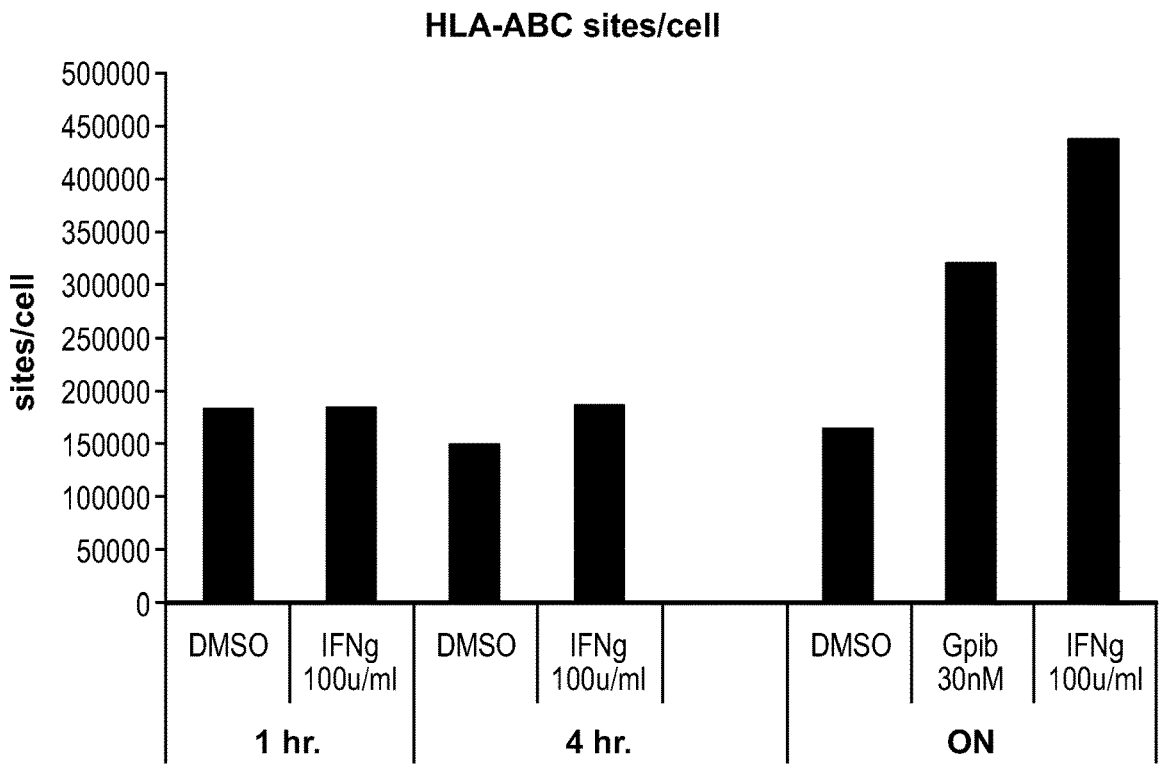
FIGS. 7A and 7B show ganetespib upregulates MHC Class I antigen expression on tumor cells.
Figure 7B:
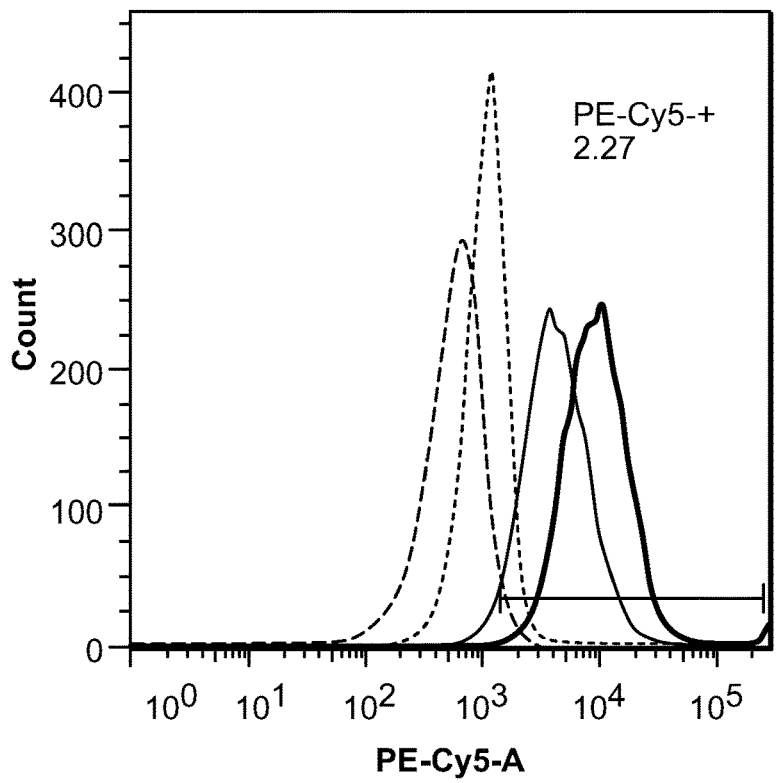

HCC827 cells were incubated with DMSO, Interferon gamma (IFNγ) or ganetespib and stained with anti MHC Class 1 antibodies and examined by flow cytometry to determine the number of molecules per cell surface. As shown in FIG. 7A, Ganetespib doubled the number of HLA-ABC molecules/cell after overnight incubation.

MC38 cells were incubated overnight with media+0.01% DMSO (dashed red line, light blue line), or media with 100 nM ganetespib (dotted red line, dark blue line). Cells were stained with an isotype control (red lines), or antibody to mouse H2-K (blue lines).

These result indicate that, in vitro, overnight treatment of MC38 cells with sublethal concentrations of ganetespib upregulates major histocompatibility antigens, especially MHC Class I.

Example 6

Figure 8:
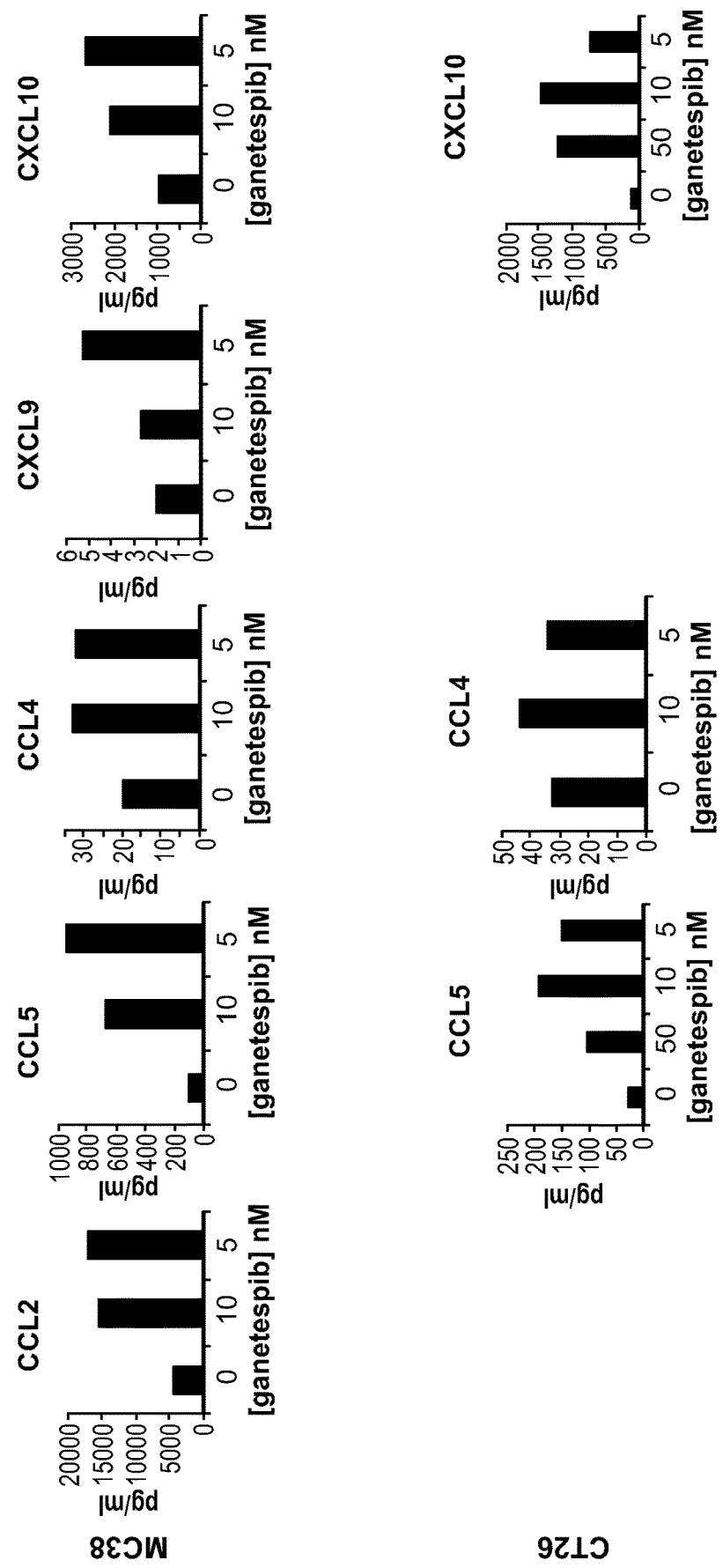
FIG. 8 demonstrates that treatment of tumor cells (MC38 and CT26) in vitro with ganetespib induces chemokine production.

MC38 or CT26 tumor cells were incubated with the indicated concentrations of ganetespib as shown in FIG. 8 in combination with 300 U/ml TNFα overnight and supernatants were collected and assayed for chemokines.

Chemokines attract lymphocytes towards the source of the chemokines, in this case the tumor cells. In some cases the chemokines seen here were also seen in the in vivo tumor experiment (first slide). The cells which would be expected to be attracted would be: CCL2: monocytes, macrophages (antigen presenting cells); CCL5: Th2 T cells; CCL4: CD8 T cells, CTL, Th1 T cells; CXCL9: Th1 T cells, NK cells; CXCL10: Th1 T cells, monocytes, NK cells, dendritic cells (antigen presenting cells).

Based on the results reflected in FIG. 8, it can be inferred that in vitro, overnight treatment of MC38 and CT26 tumors with sublethal concentration of ganetespib provokes production of chemokines by the tumor cells (CCL2, CCL5, CXCL10) which will attract antigen presenting cells, effector T cells and NK cells to the tumor.

All publications, patent applications, patents, and other documents cited herein are incorporated by reference in their entirety. In case of conflict, the present specification, including definitions, will control. In addition, the materials, methods, and examples throughout the specification are illustrative only and not intended to be limiting in any way.

We claim:

1. A method of treating cancer in a subject in need thereof, comprising administering to the subject an effective amount of a PD-1 inhibitor and an effective amount of a Hsp90 inhibitor, or a tautomer, or a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole or 5-hydroxy-4-(5-hydroxy-4-(1-methyl-1H-indol-5-yl)-4H-1,2, 4-triazol-3-yl)-2-isopropylphenyl dihydrogen phosphate; wherein the PD-1 inhibitor is nivolumab, pembrolizumab, pidilizumab, BMS 936559, MPDL3280A, MSB0010718C or MEDI4736; wherein the Hsp90 inhibitor is administered to the subject in a dose of about 125 mg/kg; and wherein the cancer is colon cancer or melanoma.

2. The method of claim 1, wherein the cancer is melanoma.

3. The method of claim 1, wherein the cancer is colon cancer.

4. The method of claim 1, wherein the PD-1 inhibitor binds PD-L1.

5. The method of claim 1, wherein the Hsp90 inhibitor is administered IV once weekly or twice weekly.

6. The method of claim 1, wherein the Hsp90 inhibitor is 3-(2,4-dihydroxy-5-isopropyl-phenyl)-4-(1-methyl-indol-5-yl)-5-hydroxy-[1,2,4] triazole, or a pharmaceutically acceptable salt thereof.

7. The method of claim 1, wherein the Hsp90 inhibitor is 5-hydroxy-4-(5-hydroxy-4-(1-methyl-1H-indol-5-yl)-4H-1,2,4-triazol-3-yl)-2-isopropylphenyl dihydrogen phosphate, or a pharmaceutically acceptable salt thereof.

8. The method of claim 1, wherein the PD-1 inhibitor is nivolumab.

9. The method of claim 1, wherein the PD-1 inhibitor is pembrolizumab.

10. The method of claim 1, wherein the PD-1 inhibitor and the Hsp90 inhibitor are administered separately.

11. The method of claim 1, wherein the PD-1 inhibitor and the Hsp90 inhibitor are administered simultaneously.

12. A method of treating cancer in a subject in need thereof, comprising administering to the subject an effective amount of a PD-1 inhibitor and an effective amount of a Hsp90 inhibitor, or a tautomer, or a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole or 5-hydroxy-4-(5-hydroxy-4-(1-methyl-1H-indol-5-yl)-4H-1,2,4-triazol-3-yl)-2-isopropylphenyl dihydrogen phosphate; wherein the PD-1 inhibitor is nivolumab, pembrolizumab, pidilizumab, BMS 936559, MPDL3280A, MSB0010718C or MEDI4736; wherein the Hsp90 inhibitor is administered to the subject in a dose of about 125 mg/kg; and wherein the cancer is colon cancer.

13. A method of treating cancer in a subject in need thereof, comprising administering to the subject an effective amount of a PD-1 inhibitor and an effective amount of a Hsp90 inhibitor, or a tautomer, or a pharmaceutically acceptable salt thereof, wherein the Hsp90 inhibitor is 3-(2,4-dihydroxy-5-isopropyl-phenyl)-4-(1-methyl-indol-5-yl)-5-hydroxy-[1,2,4] triazole or 5-hydroxy-4-(5-hydroxy-4-(1-methyl-1H-indol-5-yl)-4H-1,2,4-triazol-3-yl)-2-isopropylphenyl dihydrogen phosphate; wherein the PD-1 inhibitor is nivolumab, pembrolizumab, pidilizumab, BMS 936559, MPDL3280A, MSB0010718C or MEDI4736; wherein the Hsp90 inhibitor is administered to the subject in a dose of about 125 mg/kg; and wherein the cancer is melanoma.

\* \* \* \* \*